United States Patent [19]
Palmaz

[11] Patent Number: 5,382,261
[45] Date of Patent: Jan. 17, 1995

[54] METHOD AND APPARATUS FOR OCCLUDING VESSELS

[75] Inventor: Julio C. Palmaz, San Antonio, Tex.

[73] Assignee: Expandable Grafts Partnership, San Antonio, Tex.

[21] Appl. No.: 938,816

[22] Filed: Sep. 1, 1992

[51] Int. Cl.$^6$ .............. A61B 17/00; A61M 29/02
[52] U.S. Cl. .................. 606/158; 606/157; 606/194; 623/12
[58] Field of Search ............ 606/194-200, 606/157, 158; 623/1, 11, 12, 2, 3; 138/93; 600/36

[56] References Cited

U.S. PATENT DOCUMENTS

| | | | |
|---|---|---|---|
| 3,858,441 | 1/1975 | Comeau | 138/93 |
| 3,889,685 | 6/1975 | Miller et al. | 128/348 |
| 4,340,046 | 7/1982 | Cox | 138/93 |
| 4,660,603 | 4/1987 | Tash | 138/93 |
| 4,705,517 | 11/1987 | DiPisa, Jr. | 606/194 |
| 4,733,665 | 3/1988 | Palmaz | 128/343 |
| 4,739,762 | 4/1988 | Palmaz | 128/343 |
| 4,776,337 | 10/1988 | Palmaz | 128/343 |
| 4,790,313 | 12/1988 | Borrelly | 138/93 |
| 5,102,417 | 4/1992 | Palmaz et al. | 606/195 |
| 5,195,984 | 3/1993 | Schatz | 606/193 |

FOREIGN PATENT DOCUMENTS

| | | | |
|---|---|---|---|
| 0240132 | 10/1986 | German Dem. Rep. | 606/194 |
| 2410933 | 9/1974 | Germany | 606/193 |

OTHER PUBLICATIONS

"A New Vascular Occlusion Device", Nazarian et al., Abstract Cardiovascular and Interventional Radiological Society of Europe Aug. 30—Sep. 3, 1992, Barcelona, Spain.

Primary Examiner—David Isabella
Assistant Examiner—Debra S. Brittingham
Attorney, Agent, or Firm—Ben D. Tobor

[57] ABSTRACT

A vessel occluder for providing permanent occlusion of a vessel in a person utilizes a flexible closure member attached to at least one metallic radially expandable, generally tubular shaped stent, the flexible closure member having a generally tubular shaped cross-sectional configuration.

28 Claims, 2 Drawing Sheets

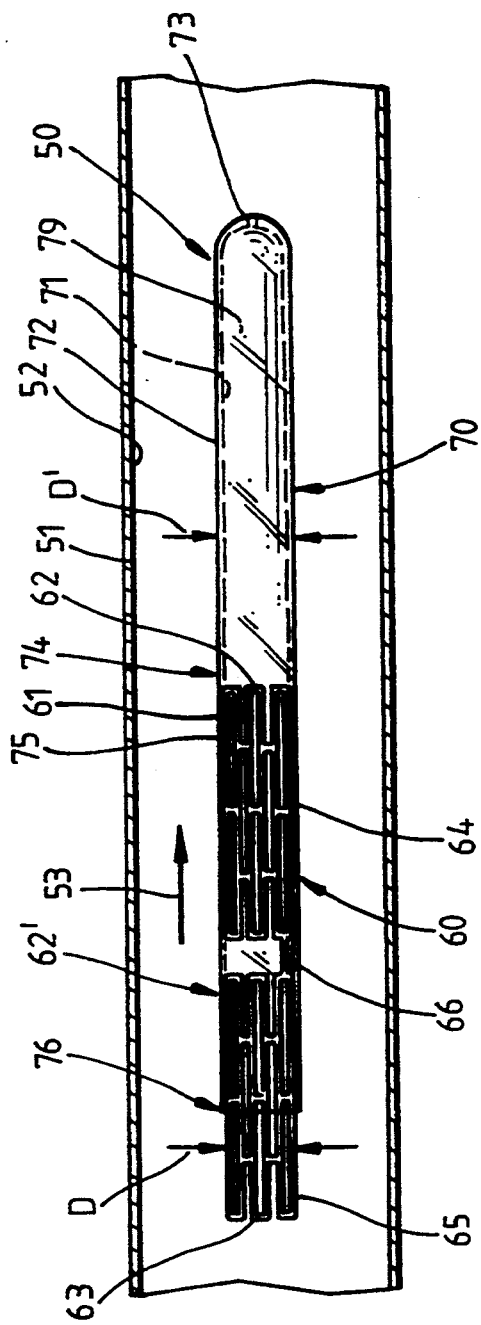
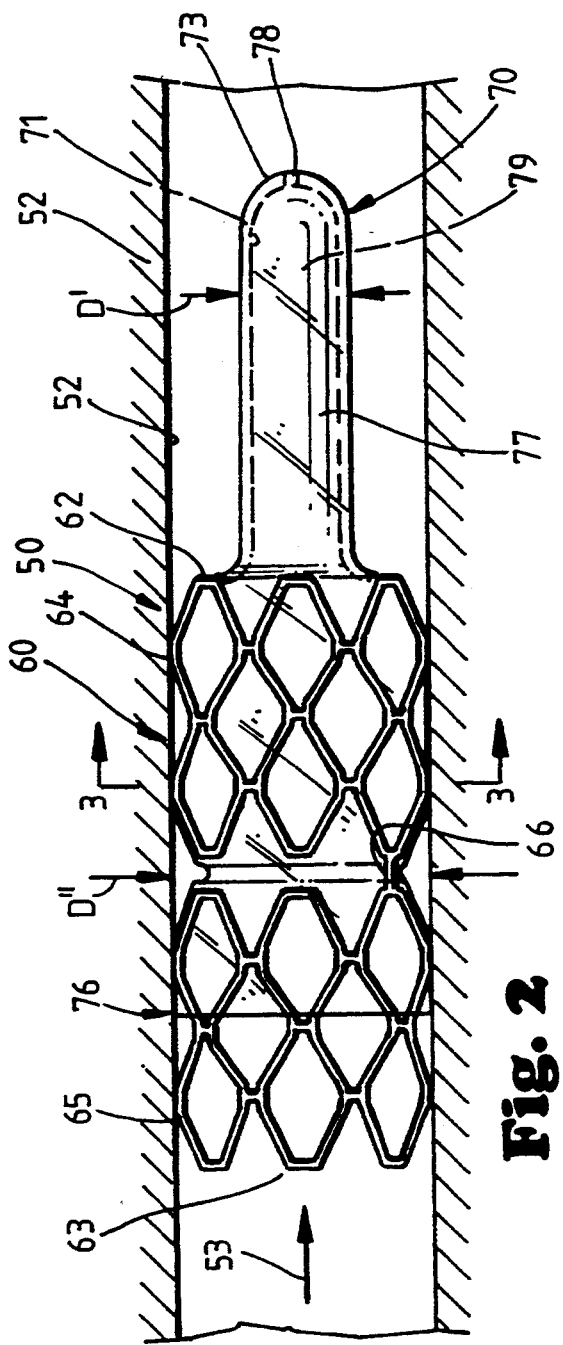
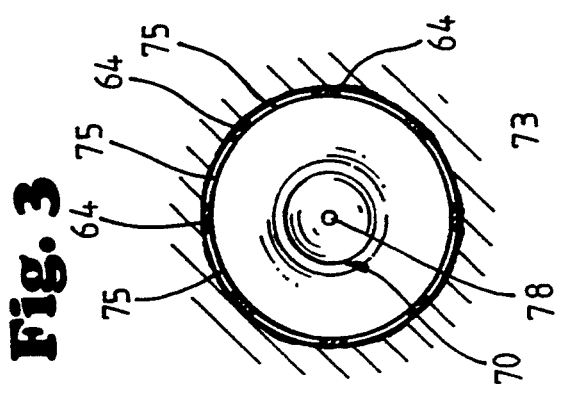

5,382,261

METHOD AND APPARATUS FOR OCCLUDING VESSELS

BACKGROUND OF THE INVENTION

1. Field of the Invention

The invention relates to a method and apparatus for providing permanent occlusion of a vessel in a person by use of a flexible closure member attached to at least one radially expandable stent.

2. Description of the Prior Art

There are many instances when it may be desirable to permanently occlude a vessel in the human body. By use of the term "vessel" it is intended to include any of the arteries and body passageways found in the human body. Examples of when permanent occlusion of a vessel might be desirable include: therapeutic occlusion, or embolization, of the renal artery; occlusion of a Blalock-Taussig Shunt; pulmonary arteriovenous fistulae and transjugular intrahepatic stent shunt occlusion; some non-vascular applications, such as therapeutic ureteric occlusion; and the occlusion of vessels feeding large cancerous tumors.

In the past, certain coiled stents or detachable balloons have been utilized for providing permanent occlusion of vessels. As to the coiled stents, it is believed that there are certain problems associated therewith, including, migration of the coiled stent within the vessel to be occluded, perforation of the vessel by the coiled stent, and failure to completely thrombose, or occlude, the vessel. Another disadvantage associated with such coiled stents is that the vessel may not be immediately occluded following placement in the vessel. Disadvantages associated with detachable occlusion balloons include premature detachment with distal embolization, or occlusion, and they are believed to require a longer period of time for the user of the device to learn how to properly use such detachable occlusion balloons.

Accordingly, prior to the development of the present invention, there has been no method and apparatus for providing permanent occlusion of a vessel which: immediately provides occlusion of the vessel; does not migrate within the vessel; does not perforate the vessel to be occluded; and is easily and efficiently used, as well as does not require a lengthy user training period. Therefore, the art has sought a method and apparatus for permanently occluding vessels which: provides immediate occlusion of the vessel; does not migrate within the vessel; does not perforate the vessel; and can be easily and efficiently used without a lengthy user training period.

SUMMARY OF THE INVENTION

In accordance with the invention, the foregoing advantages have been achieved through the present vessel occluder for providing permanent occlusion of a vessel in a person, the vessel having an inner wall surface and having a body fluid flowing therethrough. The present invention includes at least one metallic tubular shaped member, having an outer surface and first and second open ends, the tubular shaped member having a first diameter which permits intraluminal delivery of the at least one tubular shaped member into the vessel to be occluded; a flexible closure member, attached to the first open end of the at least one tubular member, which seals the first open end, the closure member having a first diameter, which is substantially the same as the at least one tubular shaped member first diameter; and the at least one tubular shaped member and at least a portion of the flexible closure member having a second expanded diameter, upon the application from the interior of the tubular shaped member of a radially outwardly extending force, which second diameter is variable and controlled by the amount of force applied to the tubular shaped member, which force deforms at least a portion of the at least one tubular shaped member to retain the at least one tubular shaped member and the portion of the closure member with the second expanded diameter, whereby the closure member is disposed in sealing engagement with the inner wall surface of the vessel and occludes the vessel to prevent the body fluid from flowing past the closure member.

A feature of the present invention is that the flexible closure member may be formed of a bio-compatible material which is disposed over at least a portion of the at least one tubular shaped member. A further feature of the present invention is that the flexible closure member may be formed integral with the portion of the at least one tubular shaped member. An additional feature of the present invention is that the flexible closure member may be formed as a coating of the bio-compatible material upon the portion of the at least one tubular shaped member, and the coating may cover approximately two-thirds of the outer surface of the at least one tubular shaped member.

A further feature of the present invention is that the flexible closure member may have inner and outer surfaces and a generally tubular shaped cross-sectional configuration with first and second ends, the first closure member end being closed and the second closure member end being open and in fluid communication with the first open end of at least one tubular shaped member, and the outer surfaces of the at least one tubular shaped member and the closure member being sealed with respect to each other. Another feature of the present invention is that the first closure member end may have a generally bullet-shaped configuration.

A further feature of the present invention is that the flexible closure member may define a variable volume of space dependent upon a pressure force exerted by the body fluid upon the inner surface of the closure member. Another feature of the present invention is that first and second tubular shaped members may be utilized, which are connected by at least one flexible connector member, the flexible closure member being attached to at least the first end of the first tubular shaped member.

In accordance with the invention, the foregoing advantages have also been achieved through the present method for permanently occluding a vessel in a person, the vessel having an inner wall surface and a body fluid flowing therethrough. This aspect of the present invention may include the steps of: attaching a flexible closure member to a first open end of at least one metallic, generally tubular shaped, radially expandable stent, the flexible closure member being provided with a generally tubular shaped cross-sectional configuration, with inner and outer wall surfaces and first and second ends, the first closure member end being closed and the second closure member end being open and in fluid communication with the first open end of the stent; disposing the at least one stent and flexible closure member upon a catheter; inserting the flexible closure member, at least one stent and catheter within the vessel to be occluded; and expanding the at least one stent to permanently dispose at least a portion of the outer surface of the flexible closure member in a sealing relationship with the inner wall surface of the vessel, whereby the vessel is occluded and body fluid is prevented from flowing past the flexible closure member.

A further feature of this aspect of the present invention may include the step of passing a guide wire through the first closed end of the flexible closure member prior to inserting the flexible closure member, at least one stent, and catheter within the vessel to be occluded. A further feature of the present invention is that the body fluid exerts a pressure force upon the inner wall surface of the flexible closure member after the flexible closure member is permanently disposed in the vessel, and further including the step of dampening the pressure force exerted upon the inner wall surface of the flexible closure member. A feature of this aspect of the present invention is that the pressure force may be dampened by permitting the flexible closure member to expand in response to the pressure force.

Another feature of the present invention may include the step of attaching the flexible closure member to the at least one stent by forming the flexible closure member integral with the at least one stent. An additional feature of the present invention is that the second end of the flexible closure member may be formed integral with the at least one stent by coating at least a portion of the at least one stent with a bio-compatible material which forms the flexible closure member to embed the portion of the at least one stent in the bio-compatible material. A further feature of the present invention may include the step of forming the outer wall surface of the first closure member end with a generally bullet-shaped configuration.

The vessel occluder and method for providing permanent occlusion of a vessel in a person of the present invention, when compared with previously proposed prior art occlusion devices and methods, have the advantages of: providing immediate occlusion of the vessel; not migrating within the vessel; not perforating the vessel; and being easily and efficiently used without a lengthy user training period.

BRIEF DESCRIPTION OF THE DRAWINGS

In the drawings:

FIG. 1 is a side view of a vessel occluder of the present invention, the vessel occluder being illustrated with a first diameter which permits intraluminal delivery of the vessel occluder into a vessel;

FIG. 2 is a partial cross-sectional front view of the vessel occluder of the present invention in its expanded configuration within a vessel;

FIG. 3 is a cross-sectional view along line 3—3 of FIG. 2; and

Figure 4:
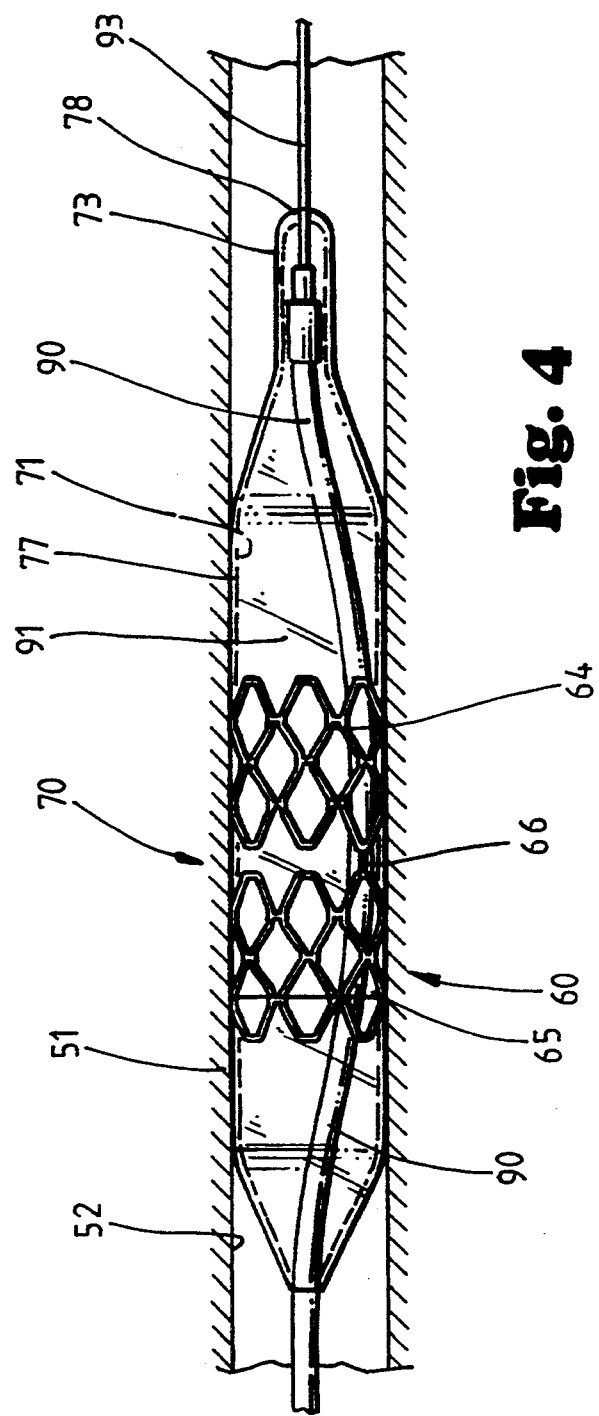
FIG. 4 is a partial cross-sectional front view of the vessel occluder of the present invention disposed upon a catheter, and illustrating the expansion of the vessel occluder.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

In FIG. 1, the vessel occluder 50 of the present invention, for providing permanent occlusion of a vessel 51 in a person (not shown) is illustrated, the vessel 51 having an inner wall surface 52 and having a body fluid, represented by arrow 53, flowing through vessel 51. Vessel occluder 50 is shown to generally comprise at least one metallic tubular shaped member 60 and a flexible closure member 70 attached to the tubular shaped member 60. Tubular shaped member, or stent, 60 has an outer surface 61 and first and second open ends 62, 63. As seen in FIG. 1, tubular shaped member 60 has a first diameter D which permits intraluminal delivery of the at least one tubular shaped member 60 into vessel 51 to be occluded. Tubular shaped member, or stent 60, may be any radially expandable, generally tubular shaped stent; however, it is preferred that stent 60 be a PAL-MAZ ™ balloon-expandable stent manufactured by Johnson & Johnson Interventional Systems Company, as also illustrated and described in U.S. Pat. Nos. 4,733,665; and 4,739,762 to Julio C. Palmaz, which patents are incorporated herein by reference. In the preferred embodiment of vessel occluder 50 of the present invention, the at least one tubular shaped member, or stent, 60 includes first and second tubular shaped members 64, 65 which are connected by at least one flexible connector member 66, the flexible closure member 70 being attached to at least the first end 62 of the first tubular shaped member 64, as will hereinafter be described in further detail. The stent, 60 comprised of first and second stents 64, 65, preferably has the construction of the expandable intraluminal graft, or stent, illustrated in U.S. Pat. No. 5,102,417, issued Apr. 7, 1992 or U.S. patent application Ser. No. 07/657,296, filed Feb. 19, 1991, now U.S. Pat. No. 5,195,984 which patents are incorporated herein by reference. By use of first and second stents 64, 65 flexibly connected by connector member 66, vessel occluder 50 is more capable of negotiating and passing through curved vessels.

Still with reference to FIG. 1, flexible closure member 70 is preferably attached to at least a portion, or the first open end, 62 of stent 60, which in turn provides a seal to the first open end 62 of stent 60, as will be hereinafter described in further detail. Flexible closure member 70 preferably has a first diameter D′, which is substantially the same as the first diameter D of stent 60. Preferably, flexible closure member 70 has a generally tubular shaped cross-sectional configuration with inner and outer wall surfaces 71, 72, and first and second ends 73, 74. The first end 73 is closed and has a generally bullet-shaped configuration. By use of the term "bullet-shaped" is meant that the first end 73 resembles the curved end surface of a conventional bullet. The second end 74 of closure members 70 is open and in fluid communication with the first open end 62 of stent 60.

Flexible closure member 70 may be attached to stent 60 in any suitable manner which permits flexible closure member 70 to operate in the manner to be hereafter described, such as by forming closure member 70 as a sleeve placed over at least the first open end portion 62 of stent 60. Preferably, flexible closure member 70 is formed of a bio-compatible material, such as medical grade silicone which may be obtained from Dow Corning Corporation. The bio-compatible material, or silicone, may be disposed over at least a portion of stent 60, or over its first open end 62. Preferably, flexible closure member 70 is formed integral with at least the first open end portion 62 of stent 60, as by being formed as a coating 75 of the bio-compatible material, or silicone, over the first open end portion 62 of stent 60, whereby the first open end portion 62 of stent 60 becomes embedded within the bio-compatible material (FIG. 3). Preferably, coating 75 covers approximately two-thirds of the outer surface 61 of stent 60, the end of coating 75 being indicated at 76. In connection with the preferred embodiment, coating 75 covers the entire first stent 64 and a portion of the second stent 65, whereby the entire first stent 64, flexible connector member 66, and the first end portion 62' of second stent 65 are embedded within coating 75. In manufacturing vessel occluder 50 to have the configuration previously described, a conventional mandrel (not shown) may be utilized to have the silicone coated upon it to provide the inner wall surface 71 and first closed end 73 of flexible closure member 70 during the coating process; or any other conventional molding process can be utilized to integrally form and attach flexible closure member 70 to stent 60 to achieve the configuration illustrated in FIG. 1. By way of example, a PALMAZ ™ stent PS 20 could be utilized for stent 60 with a first diameter D of 3.3 mm. and a length of 20 mm. and can be coated with medical grade silicone to form a flexible closure member 70, wherein the distance between the first end 73 of the closure member 70 and the first end 62 of the at least one stent 60 is 10 mm., or approximately one-half the distance between the first and second ends 62, 63 of the at least one stent 60, whereby the total length of vessel occluder 50 would be approximately 30 mm.

With reference to FIGS. 2 and 3, vessel occluder 50 is illustrated in the configuration it would have within vessel 51 after the at least one tubular shaped member, or stent, 60 has been expanded into a second expanded diameter D'', in a manner which will be hereinafter described. A catheter 90 having an expandable, inflatable portion, or balloon 91 associated therewith (FIG. 4) may be utilized to apply from the interior of tubular shaped member, or stent, 60 a radially outwardly extending force to expand stent 60 into its second expanded diameter D''. The second diameter D'' is variable and controlled by the amount of force applied to the interior of the stent 60, or the amount of inflation of balloon 91 associated with catheter 90. The force provided by the expansion of balloon 91 deforms at least a portion of the stent 60, so that it retains its second expanded diameter D''. Because of the construction of flexible closure member 70, whereby at least a portion of flexible closure member 70, or that part of the coating 75 disposed between first open end portion 62 of stent 60 and point 76, also assumes the second expanded diameter D'', and that portion of the coating 75 is disposed in sealing engagement with the inner wall surface 52 of vessel 51. As illustrated in FIG. 2, a portion 77 of flexible closure member 70, disposed between the first open end portion 62 of stent 60 and the first closed end 73, retains the first diameter D', which is also illustrated in FIG. 1. Accordingly, because of the sealing engagement of coating 75 against the inner wall surface 52 of vessel 51, in combination with the remaining portion 77 and closed first end 73 of flexible closure member 70, the vessel 51 is occluded and the passage of fluid 53 flowing past the flexible closure member 70 is prevented. The uncoated second end portion 65 of stent 60, or second end 63 of stent 65, having been firmly expanded against the inner surface 52 of vessel 51, securely and permanently disposes vessel occluder 50 in its desired position with respect to vessel 51.

With reference to FIGS. 2–4, vessel occluder 50 is shown disposed upon the expandable, inflatable portion, or balloon, 91 of catheter 90, after stent 60 has been expanded by balloon 91. As illustrated in FIG. 4, as balloon 91 of catheter 90 is expanded, the leading portion 77 of flexible closure member 70 is also expanded. FIG. 4 illustrates a small diameter guide wire 93 which is used in connection with catheter 90 to pass vessel occluder 50 to the desired location within vessel 51 in a conventional manner. A conventional vascular sheath (not shown) and introducer tube (not shown) may be used to protect vessel occluder 50 and catheter 90 during a conventional insertion procedure through a haemostatic valve (not shown). In order to pass the guide wire 93 through the first closed end 73 of flexible closure member 70, a small hole 78 may be formed in the bullet-shaped tip end portion 73 of flexible closure member 70, as by forcing the stiff end of a small diameter guide wire, such as a 0.035 inch guide wire through end 73. After vessel occluder has been permanently disposed within vessel 51, as previously described, catheter 90 and guide wire 93 are removed in a conventional manner, after the balloon 91 has been deflated. After deflation of balloon 91, leading portion 77 of closure member 70 assumes its configuration illustrated in FIG. 2. Because of the flexible construction of the flexible closure member 70, after the guide wire 93 has been removed, opening 78 closes in upon itself in a sealing relationship, whereby flexible closure member 70 can provide the desired occlusion of vessel 51.

With reference to FIG. 2, it should be noted that upon expansion of stent 60 and vessel occluder 50 being permanently disposed within vessel 51, the body fluid 53 flowing toward flexible closure member 70 exerts a pressure force upon the inner surface 71 of flexible closure member 70. This pressure force can be caused by blood pulse pressure caused by systolic contraction. Flexible closure member 70 defines a variable volume of space 79, in that the flexible construction of flexible closure member 70 can be enlarged, or expanded, in response to the pressure force exerted by the body fluid 53 upon the inner surface 71 of flexible closure member 70. The pressure force exerted by body fluid 53 is thus dampened by the expansion of the flexible closure member 70 in response to the pressure force exerted upon inner surface 71 of flexible closure member 70.

It is to be understood that the invention is not limited to the exact details of construction, operation, exact materials or embodiment shown and described, as obvious modifications and equivalents will be apparent to one skilled in the art. For example, a portion of the flexible closure member could have a bellows type configuration. Accordingly, the invention is therefore the be limited only by the scope of the appended claims.

What is claimed is:

1. A vessel occluder for providing permanent occlusion of a vessel in a person, the vessel having an inner wall surface and having a body fluid flowing therethrough, comprising:

at least one metallic tubular shaped member, having an outer surface, an interior and first and second open ends, the tubular shaped member having a first diameter which permits intraluminal delivery of the at least one tubular shaped member into the vessel to be occluded;

a flexible closure member, attached to the first open end of the at least one tubular member, which seals the first open end, the closure member having a first diameter, which is substantially the same as the at least one tubular shaped member first diameter; and the at least one tubular shaped member and at least a portion of the flexible closure member having a second expanded permanent diameter, upon the application from the interior of the tubular shaped member of a radially outwardly extending force, which second diameter is variable and controlled by an amount of force applied to the tubular shaped member, which force deforms at least a portion of the at least one tubular shaped member to permanently retain the at least one tubular shaped member and the portion of the closure member with the second expanded permanently diameter, whereby the closure member is disposed in sealing engagement with the inner wall surface of the vessel and occludes the vessel to prevent the body fluid from flowing past the closure member.

2. The vessel occluder of claim 1, wherein the flexible closure member is formed of a bio-compatible material which is disposed over at least a portion of the at least one tubular shaped member.

3. The vessel occluder of claim 2, wherein the flexible closure member is formed integral with the portion of the at least one tubular shaped member.

4. The vessel occluder of claim 3, wherein the flexible closure member is formed as a coating of the bio-compatible material upon the portion of the at least one tubular shaped member.

5. The vessel occluder of claim 4, wherein the coating covers approximately two-thirds of the outer surface of the at least one tubular shaped member.

6. The vessel occluder of claim 1, wherein the flexible closure member has inner and outer surfaces and a generally tubular shaped cross-sectional configuration with first and second ends, the first closure member end being closed and the second closure member end being open and in fluid communication with the first open end of the at least one tubular shaped member, and the outer surfaces of the at least one tubular shaped member and the closure member being sealed with respect to each other.

7. The vessel occluder of claim 6, wherein the first closure member end has a generally bullet-shaped configuration.

8. The vessel occluder of claim 6, wherein the first closure member end has a small opening formed therein, adapted to permit a guide wire to pass therethrough and adapted to close in upon itself in a sealing relationship upon the guide wire being removed.

9. The vessel occluder of claim 6, wherein the flexible closure member defines a variable volume of space dependent upon a pressure force exerted by the body fluid upon the inner surface of the closure member.

10. The vessel occluder of claim 1, including first and second tubular shaped members connected by at least one flexible connector member, the flexible closure member being attached to at least the first end of the first tubular shaped member.

11. A method for permanently occluding a vessel in a person, the vessel having an inner wall surface and a body fluid flowing therethrough, comprising the steps of:

attaching a flexible closure member to a first open end of at least one metallic, generally tubular shaped, radially expandable stent, the flexible closure member being provided with a generally tubular shaped cross-sectional configuration, with inner and outer wall surfaces and first and second ends, the first closure member end being closed and the second closure end being open and in fluid communication with the first open end of the stent;

disposing the at least one stent and flexible closure member upon a catheter;

inserting the flexible closure member, at least one stent and catheter within the vessel to be occluded; and expanding the at least one stent to permanently dispose at least a portion of the outer surface of the flexible closure member in a sealing relationship with the inner wall surface of the vessel, whereby the vessel is occluded and body fluid is prevented from flowing past the flexible closure member.

12. The method of claim 11, including a step of passing a guide wire through the first closed end of the flexible closure member, prior to inserting the flexible closure member, at least one stent, and catheter within the vessel to be occluded.

13. The method of claim 12, including a step of removing the guide wire and catheter after the at least one stent has been expanded.

14. The method of claim 11, wherein the body fluid exerts a pressure force upon the inner wall surface of the flexible closure member after the flexible closure member is permanently disposed in the vessel, and further including a step of dampening the pressure force exerted upon the inner wall surface of the flexible closure member.

15. The method of claim 14, wherein the pressure force is dampened by permitting the flexible closure to expand in response to the pressure force.

16. The method of claim 14, including a step of attaching the closure member to the at least one stent by forming the flexible closure member integral with the at least one stent.

17. The method of claim 16, wherein the second end of the flexible closure member is formed integral with the at least one stent by coating at least a portion of the at least one stent with a bio-compatible material, which forms the flexible closure member, to embed the portion of the at least one stent in the bio-compatible material.

18. The method of claim 11, including a step of forming the outer wall surface of the first closure member end with a generally bullet-shaped configuration.

19. An apparatus for providing permanent occlusion of a vessel in a person, the vessel having an inner wall surface and having a body fluid flowing therethrough comprising:

a catheter, having an expandable, inflatable portion associated therewith, at least one metallic tubular shaped member, having an outer surface an interior and first and second open ends, the tubular shaped member having a first diameter which permits intraluminal delivery of the at least one tubular shaped member into the vessel to be occluded, the at least one tubular shaped member being disposed upon the expandable, inflatable portion of the catheter;

a flexible closure member, attached to the first open end of the at least one tubular member, which seals the first open end, the closure member having a first diameter, which is substantially the same as the at least one tubular shaped member first diameter; and the at least one tubular shaped member and at least a portion of the flexible closure member having a second expanded diameter, upon an application from the interior of the tubular shaped member of a radially outwardly extending force, which second diameter is variable and controlled by an amount of force applied to the tubular shaped member, which force deforms at least a portion of the at least one tubular shaped member to retain the at least one tubular shaped member and the portion of the closure member with the second expanded diameter, whereby the closure member is disposed in sealing engagement with the inner wall surface of the vessel and occludes the vessel to prevent the body fluid from flowing past the closure member.

20. The apparatus of claim 19, wherein the flexible closure member is formed of a bio-compatible material which is disposed over at least a portion of the at least one tubular shaped member.

21. The apparatus of claim 20, wherein the flexible closure member is formed integral with the portion of the at least one tubular shaped member.

22. The apparatus of claim 21, wherein the flexible closure member is formed as a coating of the bio-compatible mterial upon the portion of the at least one tubular shaped member.

23. The apparatus of claim 22, wherein the coating covers approximately two-thirds of the outer surface of the at least one tubular shaped member.

24. The apparatus of claim 19, wherein the flexible closure member has inner and outer surfaces and a generally tubular shaped cross-sectional configuration with first and second ends, the first closure member end being closed and the second closure member end being open and in fluid communication with the first open end of the at least one tubular shaped member, and the outer surfaces of the at least one tubular shaped member and the closure member being sealed with respect to each other.

25. The apparatus of claim 24, wherein the first closure member end has a generally bullet-shaped configuration.

26. The apparatus of claim 24, wherein the first closure member end has a small opening formed therein, adapted to permit a guide wire to pass therethrough and adapted to close in upon itself in a sealing relationship upon the guide wire being removed.

27. The apparatus of claim 24, wherein the flexible closure member defines a variable volume of space dependent upon a pressure force exerted by the body fluid upon the inner surface of the closure member.

28. The apparatus of claim 19, including first and second tubular shaped members connected by at least one flexible connector member, the flexible closure member being attached to at least the first end of the first tubular shaped member.

* * * * *

UNITED STATES PATENT AND TRADEMARK OFFICE
CERTIFICATE OF CORRECTION

PATENT NO. : 5,382,261

DATED : January 17, 1995

INVENTOR(S) : Julio C. Palmaz

It is certified that error appears in the above-identified patent and that said Letters Patent is hereby corrected as shown below:

```
In claim 1, column 6, line 64, after "interior", insert--,--.
In claim 1, column 7, line 18, delete "permanently" and insert--
permanent--.
In claim 19, column 8, line 59, after "surface", insert--,-- and
after "interior" insert--,--.
```

Signed and Sealed this

Twenty-eighth Day of November 1995

Attest:

BRUCE LEHMAN

Attesting Officer     Commissioner of Patents and Trademarks